US009706904B2

(12) United States Patent
Matsuno et al.

(10) Patent No.: US 9,706,904 B2
(45) Date of Patent: Jul. 18, 2017

(54) PACKAGING MATERIAL FOR ENDOSCOPIC TREATMENT SYSTEM AND ENDOSCOPE SYSTEM

(71) Applicant: OLYMPUS CORPORATION, Tokyo (JP)

(72) Inventors: Kiyotaka Matsuno, Sagamihara (JP); Hidenori Yoshida, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 36 days.

(21) Appl. No.: 14/857,106

(22) Filed: Sep. 17, 2015

(65) Prior Publication Data

US 2016/0073862 A1 Mar. 17, 2016

Related U.S. Application Data

(63) Continuation of application No. PCT/JP2014/061417, filed on Apr. 23, 2014.

(Continued)

(51) Int. Cl.
*A61B 1/00* (2006.01)
*A61B 19/02* (2006.01)
(Continued)

(52) U.S. Cl.
CPC ...... *A61B 1/00144* (2013.01); *A61B 18/1492* (2013.01); *A61B 19/026* (2013.01);
(Continued)

(58) Field of Classification Search
CPC ..... A61B 1/00144; A61B 50/20; A61B 50/30; A61B 50/33; A61B 18/1492;
(Continued)

(56) References Cited

U.S. PATENT DOCUMENTS 4,216,860 A * 8/1980 Heimann ............ A61M 25/002
206/364
5,318,543 A * 6/1994 Ross .................. A61B 17/0469
206/571

(Continued)

FOREIGN PATENT DOCUMENTS

EP 0 440 427 A1 8/1991
EP 0782868 A1 7/1997
(Continued)

OTHER PUBLICATIONS

International Search Report dated Jun. 17, 2014 issued in PCT/JP2014/061417.

(Continued)

*Primary Examiner* — Chun Cheung
(74) *Attorney, Agent, or Firm* — Scully, Scott, Murphy & Presser, PC

(57) ABSTRACT

An endoscopic treatment system includes: an endoscopic treatment device having an operating unit which has a distal end and a proximal end and a sheath; and a guide wire which has a coated region applied with coating at a distal end. A packaging material has a tray which maintains a predetermined position relationship between the sheath and the guide wire and holds the distal end side of the sheath in a state where the coated region of the guide wire is exposed from the distal end of the sheath. The tray is located on the distal end side of the sheath to a sheath holding portion, which holds the sheath, and has a wire accommodating portion which holds the full length of the coated region of the guide wire exposed from the distal end of the sheath in a linear form.

10 Claims, 16 Drawing Sheets

Related U.S. Application Data

(60) Provisional application No. 61/815,796, filed on Apr. 25, 2013.

(51) Int. Cl.
*A61B 18/14* (2006.01)
*A61B 50/20* (2016.01)
*A61B 50/33* (2016.01)
*A61B 50/30* (2016.01)

(52) U.S. Cl.
CPC ...... *A61B 19/0256* (2013.01); *A61B 19/0271* (2013.01); *A61B 50/20* (2016.02); *A61B 50/30* (2016.02); *A61B 50/33* (2016.02); *A61B 2018/144* (2013.01); *A61B 2019/0267* (2013.01); *A61B 2019/0278* (2013.01); *A61B 2050/3008* (2016.02); *A61B 2050/314* (2016.02)

(58) Field of Classification Search
CPC .............. A61B 19/0256; A61B 19/026; A61B 19/0271; A61B 2050/3008; A61B 2050/314; A61B 2018/144; A61B 2019/0267; A61B 2019/0278
USPC ........................................................ 206/364
See application file for complete search history.

(56) References Cited

U.S. PATENT DOCUMENTS

| | | | | |
|---|---|---|---|---|
| 5,344,011 | A * | 9/1994 | DiBernardo | A61M 25/002 206/364 |
| 5,848,691 | A | 12/1998 | Morris et al. | |
| 5,947,284 | A * | 9/1999 | Foster | A61B 50/33 206/364 |
| 6,405,863 | B1 * | 6/2002 | Dhindsa | B65D 1/36 206/370 |
| 6,533,116 | B1 * | 3/2003 | Riley | A61M 25/002 206/363 |
| 7,234,597 | B2 * | 6/2007 | Rowe | A61M 25/002 206/364 |
| 7,640,714 | B2 * | 1/2010 | Waller | A61M 25/002 206/364 |
| 8,568,373 | B2 * | 10/2013 | Kuniyasu | A61M 25/002 206/303 |
| 2003/0159966 | A1 | 8/2003 | McMichael et al. | |
| 2006/0011501 | A1 * | 1/2006 | Itou | A61M 25/002 206/370 |
| 2012/0103840 | A1 | 5/2012 | McCaffrey | |
| 2014/0110279 | A1 * | 4/2014 | Kruetzfeldt | A61F 2/2427 206/216 |
| 2014/0110296 | A1 * | 4/2014 | Terzibashian | A61M 25/002 206/438 |
| 2014/0262882 | A1 * | 9/2014 | Barnell | A61M 25/002 206/364 |
| 2015/0068941 | A1 * | 3/2015 | Caron | A61M 25/002 206/364 |
| 2015/0352316 | A1 * | 12/2015 | Terzibashian | B65D 43/16 206/363 |

FOREIGN PATENT DOCUMENTS

| | | |
|---|---|---|
| JP | H03-501570 A | 4/1991 |
| JP | H04-341276 A | 11/1992 |
| JP | H06-013847 U | 2/1994 |
| JP | H09-201369 A | 8/1997 |
| JP | 2004-275785 A | 10/2004 |
| JP | 2004-290395 A | 10/2004 |
| JP | 2008-080047 A | 4/2008 |
| JP | 2011-194128 A | 10/2011 |
| WO | WO 89/04685 A1 | 6/1989 |
| WO | WO 2010/035581 A1 | 4/2010 |

OTHER PUBLICATIONS

Japanese Office Action dated Feb. 10, 2015 issued in JP 2014-558697.

Extended Supplementary European Search Report dated Dec. 5, 2016 in European Patent Application No. 14 78 8454.8.

* cited by examiner

PACKAGING MATERIAL FOR ENDOSCOPIC TREATMENT SYSTEM AND ENDOSCOPE SYSTEM

This application is a continuation based on U.S. Patent Application No. 61/815,796 provisionally applied in the United States on Apr. 25, 2013 and PCT/JP2014/061417, filed on Apr. 23, 2014. The contents of both the United States Patent Application and the PCT Application are incorporated herein by reference.

BACKGROUND OF THE INVENTION

Field of the Invention

The present invention relates to a packaging material for an endoscopic treatment system and an endoscope system.

Background Art

In the related art, a treatment device which is used along with an endoscope has been known. For example, Japanese Patent Application Laid-Open No. 2004-275785 discloses a high-frequency incision device which is used in EST (duodenal papilla sphincter muscle resection). In the EST, it is known that a guide wire is inserted into a bile duct (or a pancreatic duct), the high-frequency incision device is removed after the guide wire is inserted, and a basket, forceps, or the like is guided to the bile duct (or the pancreatic duct) along the guide wire.

As an example of a system which inserts a guide wire into a region to be treated, for example, Japanese Patent Application Laid-Open No. 2008-80047 discloses a system in which a storage part configured to store a guide wire inserted into a region to be treated is attached to a treatment device.

An operation which guides a treatment device to a region to be treated using a guide wire is known. In this operation, the treatment device and the guide wire are respectively prepared, and an operator inserts the guide wire into the treatment device to perform the operation.

A treatment system which, for the sake of saving time and labor to insert a guide wire into a treatment device during the use of the treatment device, is provided as a set in a state where the guide wire is inserted into the treatment device in advance is known.

SUMMARY OF THE INVENTION

According to a first aspect of the invention, there is provided a packaging material which packages an endoscopic treatment system to be used in combination with an endoscope. The endoscopic treatment system includes an endoscopic treatment device having an operating part with a distal end and a proximal end and a sheath which is connected to the distal end of the operating part and in which a lumen is formed, and a guide wire which has a coated region applied with coating at a distal end of the guide wire and is inserted into the lumen of the sheath, the packaging material has a tray which holds the distal end side of the sheath in a state where a predetermined positional relationship between the sheath and the guide wire is held and the coated region of the guide wire is exposed from the distal end of the sheath, the tray has a sheath holding part which is configured to hold the sheath and a wire storage part which is placed closer to the distal end side of the sheath than the sheath holding part, and holds the full length of the coated region of the guide wire exposed from the distal end of the sheath straight, the sheath holding part has an introduction part that is positioned at a proximal end of the sheath and a bottom surface that is positioned closer than a distal end of the sheath than the introduction part, and the bottom surface is positioned lower than the introduction part in a depth direction of the tray.

According to a second aspect of the invention, in the first aspect, the sheath holding part may have a curved shape which holds the distal end side of the sheath in a curved state. The introduction part may be positioned at a proximal end side of the curved shape.

According to a third aspect of the invention, in the second aspect, the wire storage part may be arranged so as to intersect with a part of the sheath that is closer to the proximal end of the sheath than the sheath holding part of the sheath, and the sheath holding part may hold the sheath so that the part of the sheath passes through over the guide wire that is stored in the wire storage part.

According to a fourth aspect of the invention, in the first aspect, the tray may have a locking portion that is positioned closer to the proximal end of the sheath than the introduction part. The locking portion may lock the sheath so as to be detachable with respect to the depth direction of the tray.

According to a fifth aspect of the invention, in the fourth aspect, the tray may have a distal end guide wall which extends from the sheath holding part and against which the distal end portion of the sheath is pressed by a restoring force to bring the sheath into a linear state, the wire storage part may have a pair of wall surfaces which extend from the distal end guide wall and gradually increases in an interval between the pair of wall surfaces according to the distance from the distal end guide wall, and the pair of wall surfaces may be separated from the guide wire in a state where the distal end of the guide wire is arranged between the pair of wall surfaces.

According to a sixth aspect of the invention, in the fifth aspect, the distal end guide wall may have a planar shape and may hold the distal end portion of the sheath straight.

According to a seventh aspect of the invention, in the sixth aspect, the wire storage part may be formed of polypropylene.

According to an eighth aspect of the invention, in the seventh aspect, the pair of wall surfaces may extend from the bottom surface, and the packaging material may further include a lid member which has a top surface portion facing the bottom surface.

According to a ninth aspect of the invention, in the eighth aspect, the endoscopic treatment system may further include a guide wire holder which is formed so that a tube body in which the guide wire is stored is wound circumferentially, and a fixing member which connects the operating part to the guide wire holder such that the distal end and the proximal end of the operating part of the endoscopic treatment device are placed outside the circumference of the guide wire holder, and the tray may support the operating part and the guide wire holder in a state where a predetermined positional relationship between the operating part and the guide wire holder is held.

According to a tenth aspect of the invention, in the ninth aspect, the sheath holding part and the wire storage part may be positioned inside of a circumference of a circle of the guide wire holder in a state where the tray holds the operating part and the guide wire holder.

An endoscope system according to an eleventh aspect of the invention includes an endoscopic treatment device having an operating part with a distal end and a proximal end and a sheath which is connected to the distal end of the operating part and in which a lumen is formed, a guide wire which has a coated region applied with coating at a distal end and is inserted into a lumen of the sheath, and the packaging material of the first aspect.

DESCRIPTION OF THE PREFERRED EMBODIMENTS

Figure 1:
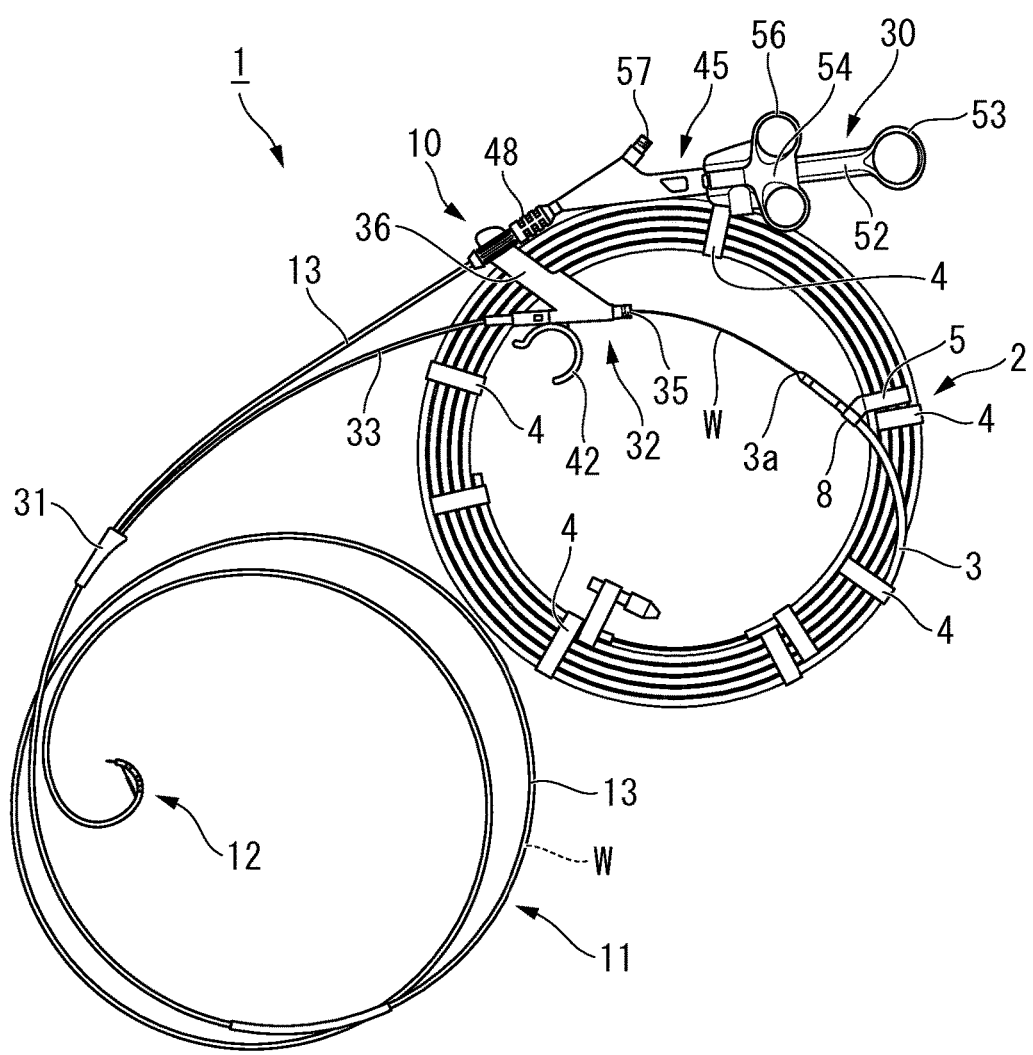
FIG. 1 is an overall view illustrating an endoscopic treatment system which is packaged by a packaging material according to an embodiment of the invention.

An endoscopic treatment system according to an embodiment of the invention will be described. FIG. 1 is an overall view illustrating an endoscopic treatment system of this embodiment.

As illustrated in FIG. 1, an endoscopic treatment system 1 is a system which has a guide wire W and a high-frequency incision device (endoscopic treatment device) 10, and is provided in a state where the guide wire W is attached to the high-frequency incision device 10 in advance. The guide wire W is a wire material which is provided to guide the high-frequency incision device 10 to a region to be treated. The guide wire W is a wire material which is flexible and is excellent in a torque transmission property. The guide wire W is stored in a guide wire holder 2 which is formed by winding a flexible tube body 3 circumferentially, and is wound along the tube body 3. The guide wire W is delivered from an opening 3a provided at one end of the tube body 3, and is inserted into the high-frequency incision device 10 through a below-described wire insertion port 35 provided in the high-frequency incision device 10. The distal end of the guide wire W is provided in a state of being delivered from the distal end of the insertion part 11 of the high-frequency incision device 10.

The distal end of the guide wire W is applied with hydrophilic lubricating coating for the sake of increasing an insertion property for a biological tissue.

In this embodiment, the tube body 3 is wound in a spiral shape on the same plane. The tube body 3 is maintained in a spiral shape by a plurality of clips 4. The tube body 3 is provided with a holding device 5 which defines the position of the opening 3a of the tube body 3, through which the guide wire W is delivered.

The material of the tube body 3 is not particularly limited. For example, the tube body 3 is formed of resin, such as polytetrafluoroethylene (PTFE), tetrafluoroethylene-hexafluoropropylene resin (FEP), polyethylene, polyolefin, polyamide, vinyl chloride, latex, natural rubber, polysulphone, polyphenylsulfon, polyetherimide, POM, PEEK, polycarbonate, or ABS, or a synthetic resin material thereof.

Figure 2:
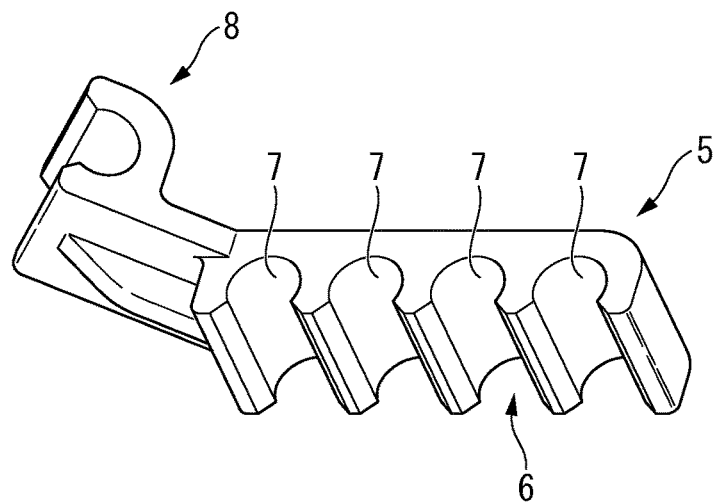
FIG. 2 is a perspective view of a holding device which is attached to a guide wire holder of the endoscopic treatment system.
Figure 3:
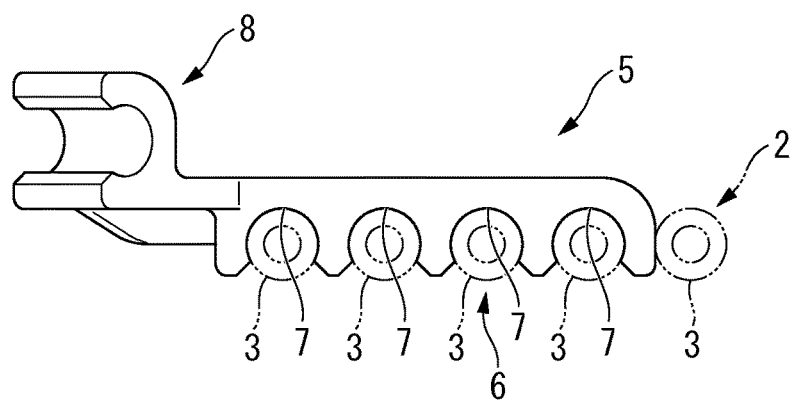
FIG. 3 is a plan view of the holding device.
Figure 4:
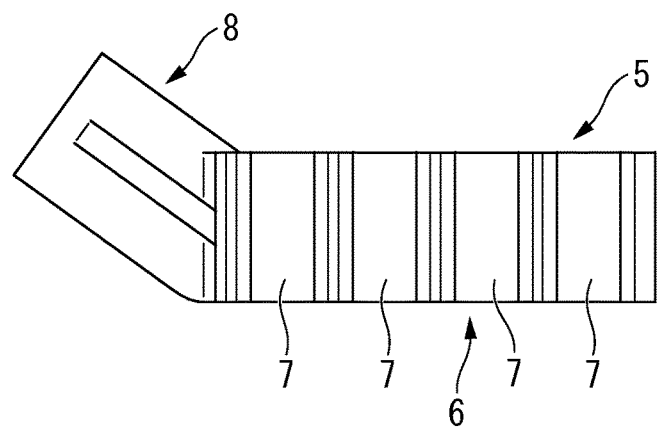
FIG. 4 is a front view of the holding device.

FIG. 2 is a perspective view of the holding device 5 which is attached to the guide wire holder 2 of the endoscopic treatment system 1. FIG. 3 is a plan view of the holding device 5. FIG. 4 is a front view of the holding device 5.

As illustrated in FIGS. 1 to 4, the holding device 5 has a first concave portion 6 and a second concave portion 8 which are engaged with the outer surface of the tube body 3. A part of an intermediate portion of the tube body 3 wound circumferentially is engaged with the first concave portion 6. In this embodiment, the first concave portion 6 is provided with a plurality of adjacent concave portions 7 (in the illustrated example, four) having the same shape. The tube body 3 wound circumferentially is engaged with a plurality of concave portions 7 by friction. As illustrated in FIG. 3, each concave portion 7 in the first concave portion 6 has an arc-like concave shape which covers half or more the circumference of the outer surface of the tube body 3 in the cross-section of the tube body 3 in a radial direction.

When engaging the tube body 3 with the first concave portion 6, the tube body 3 is pressed in the first concave portion 6. With this, the tube body 3 is elastically deformed and gets into each concave portion 7 of the first concave portion 6. Inside the first concave portion 6, the tube body 3 is restored to the original shape. For this reason, inside the tube body 3 which gets into the first concave portion 6, a space where the guide wire W is able to be freely advanced and retracted is provided. If the tube body 3 is pulled out in the radial direction of the tube body 3 with respect to the first concave portion 6, the tube body 3 is able to be detached from the first concave portion 6.

In this embodiment, in the guide wire holder 2 (see FIGS. 1 and 3) in which the tube body 3 is wound five times, the holding device 5 is provided with four adjacent concave portions 7 to hold four adjacent tube bodies 3. The number of concave portions 7 which are formed in the first concave portion 6 may be smaller than the number of turns of the tube body 3. With this, the first concave portion 6 does not further protrude outward from the outer circumference of the tube body 3, and the guide wire holder 2 becomes compact.

That is, the number of concave portions 7 which are formed in the first concave portion 6 may be equal to or greater than 2 and less than the number of turns of the tube body 3.

As illustrated in FIGS. 1 to 3, the second concave portion 8 is a concave portion with which the vicinity of the opening 3a of the tube body 3, through which the guide wire W is delivered, is engaged. The second concave portion 8 has an arc-like concave shape which covers half or more the circumference of the outer surface of the tube body 3 in the cross-section of the tube body 3 in the radial direction. The second concave portion 8 has a concave shape which forms an arc, in which an opening is directed to the inside of a circumference formed by the tube body 3 in a state where the first concave portion 6 is attached to the tube body 3. The second concave portion 8 may form an arc in which an opening is directed in a direction intersecting a plane, on which a circumference formed by the tube body 3 exists. For example, the second concave portion 8 may form an arc in which an opening is directed in a direction perpendicular to a plane, on which a circumference formed by the tube body 3 exists.

As a first attachment form in this embodiment, the second concave portion 8 places the opening 3a, through which the guide wire W is delivered, further inside than the tube body 3 placed on the innermost circumferential side of the tube body 3 wound circumferentially (in this embodiment, spirally) (see FIG. 1). That is, in the outermost circumferential portion of the tube body 3, the tube body 3 is bent by the holding device 5 to face the inner circumference from the outer circumference.

Figure 14:
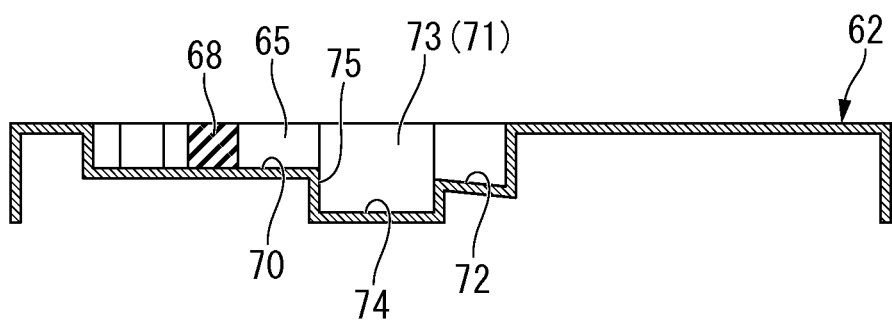
FIG. 14 is a sectional view taken along the line A-A of FIG. 12.

As a second attachment form in this embodiment, the second concave portion 8 places the opening 3a further outside than the tube body 3 placed on the outermost side out of the tube body 3 wound circumferentially (in this embodiment, spirally) (see FIG. 14).

The attachment direction of the first concave portion 6 to the tube body 3 changes to attach the holding device 5 to the tube body 3, thereby switching between the first attachment form and the second attachment form.

Figure 5:
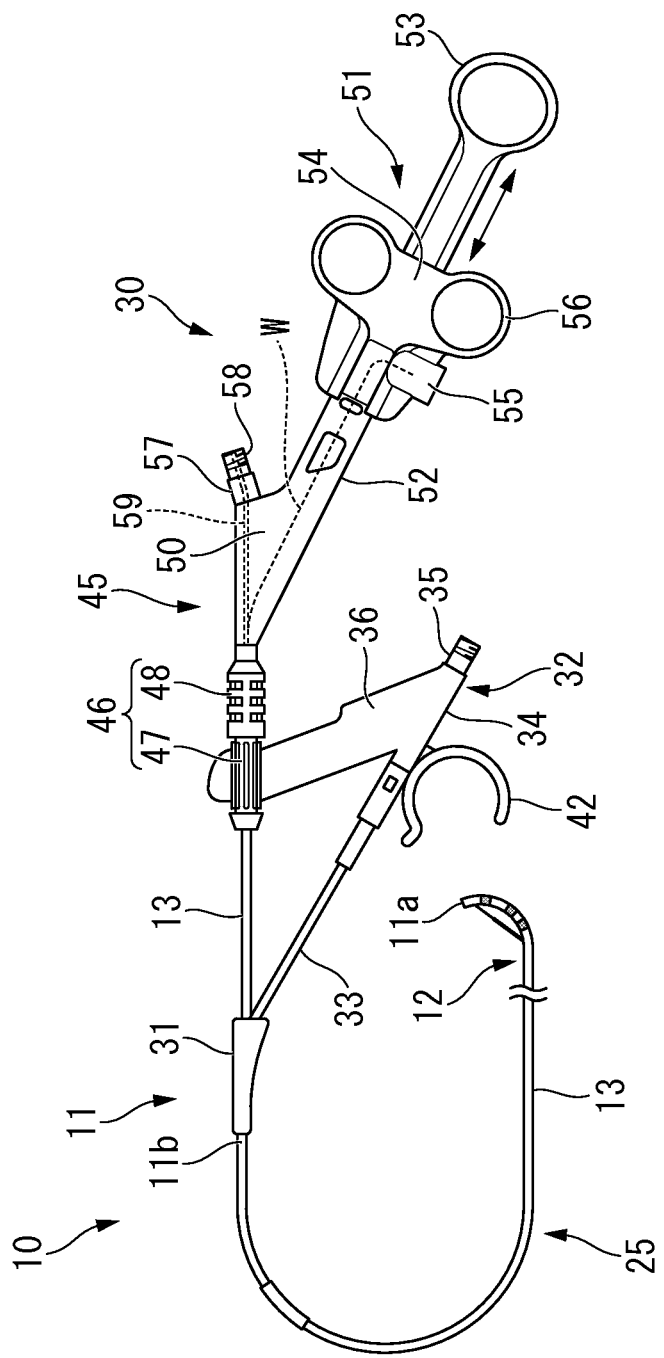
FIG. 5 is a side view of a high-frequency incision device in the endoscopic treatment system.
Figure 6:
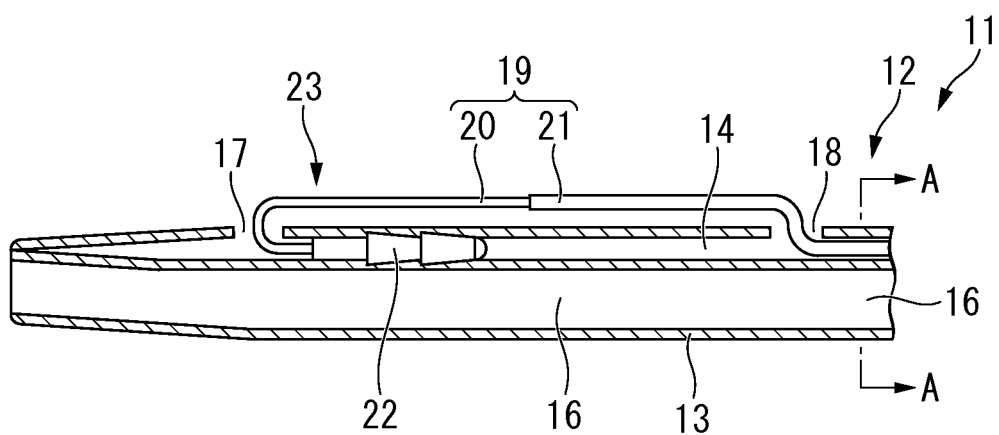
FIG. 6 is a sectional view illustrating an incision part in the endoscopic treatment system.
Figure 7:
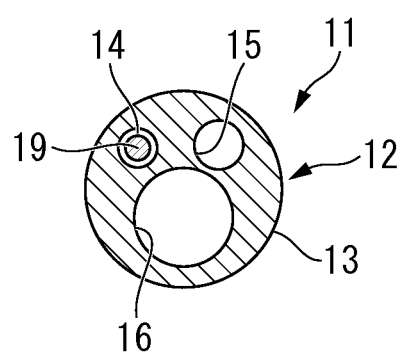
FIG. 7 is a sectional view of a multi-lumen tube in the endoscopic treatment system.

Next, the configuration of the high-frequency incision device 10 will be described. FIG. 5 is a side view of a high-frequency incision device in the endoscopic treatment system. FIG. 6 is a sectional view illustrating an incision part in the endoscopic treatment system. FIG. 7 is a sectional view of a multi-lumen tube in the endoscopic treatment system.

As illustrated in FIG. 5, the high-frequency incision device 10 has an insertion part 11 and an operating part 30.

The insertion part 11 is a flexible elongated member which has a distal end 11a and a proximal end 11b. The insertion part 11 has an incision part 12 which incises a biological tissue, and a sheath part (sheath) 25 which guides the incision part 12 to a region to be incised.

As illustrated in FIGS. 6 and 7, the incision part 12 is formed by a multi-lumen tube 13 having three lumens in one tube. The three lumens in the multi-lumen tube 13 are formed to have different inner diameters. In this embodiment, a conductive knife wire 19 which is used to incise a biological tissue is inserted into a lumen (first lumen 14) having the smallest inner diameter. Of the three lumens, a lumen (second lumen 15) having the second smallest inner diameter is used as a conduit which is used to supply a fluid, such as a contrast medium. Of the three lumens, a lumen (third lumen 16) having the largest inner diameter is used as a conduit into which the guide wire W is inserted.

At the sidewall on the distal end side of the multi-lumen tube 13, two slits 17 and 18 which communicate with the first lumen 14 are formed. The two slits 17 and 18 are arranged to be separated from each other in the longitudinal axis direction of the multi-lumen tube 13. The knife wire 19 is inserted into the slits 17 and 18. That is, a part on the distal end side of the knife wire 19 is arranged outside the multi-lumen tube 13 through the slits 17 and 18 formed at the sidewall of the multi-lumen tube 13.

The knife wire 19 has a conductive element wire 20, and an insulating coating 21 which coats a part of the element wire 20. A knife chip 22 which is used to fix the knife wire 19 to the distal end of the first lumen 14 is connected to the distal end of the knife wire 19. The knife chip 22 is pressed into the slit 17 placed on the distal end side of the two slits 17 and 18 formed in the multi-lumen tube 13 and is fixed inside the first lumen 14.

In the knife wire 19, a part on the proximal end side of the knife chip 22 is an exposed portion 23 which has no insulating coating 21. The exposed portion 23 is set in a range placed outside the multi-lumen tube 13 out of the full length of the knife wire 19.

The insulating coating 21 is provided on the proximal end side to the exposed portion 23 in the knife wire 19. The insulating coating 21 is formed by coating for insulation on the outer circumferential surface of the element wire 20 of the knife wire 19.

The proximal end side to the exposed portion 23 in the knife wire 19 extends toward the proximal end side of the insertion part 11. The proximal end of the knife wire 19 is connected to the operating part 30 (see FIG. 5).

As illustrated in FIG. 5, the sheath part 25 is provided on the proximal end side of the incision part 12. The sheath part 25 is an extended portion of the multi-lumen tube 13 constituting the incision part 12 toward the proximal end side. In this embodiment, the incision part 12 and the sheath part 25 have the multi-lumen tube 13. With this, similarly to the incision part 12, the sheath part 25 has the first lumen 14, the second lumen 15, and the third lumen 16 formed therein.

As illustrated in FIG. 5, the operating part 30 is branched into a first operating part 32 and a second operating part 45 by a first branch part 31 connected to the multi-lumen tube 13 constituting the sheath part 25. The first operating part 32 has a flexible guide wire tube 33 which is pulled out from the first branch part 31, and a guide wire insertion part 34 which is used to insert the guide wire W. In this embodiment, in the operating part 30, the side connected to the sheath part 25 is the distal end side in the operating part 30.

In the guide wire tube 33, the distal end side communicates with the third lumen 16 (see FIG. 7) in the first branch part 31, and the proximal end side is fixed to the guide wire insertion part 34.

Figure 8:
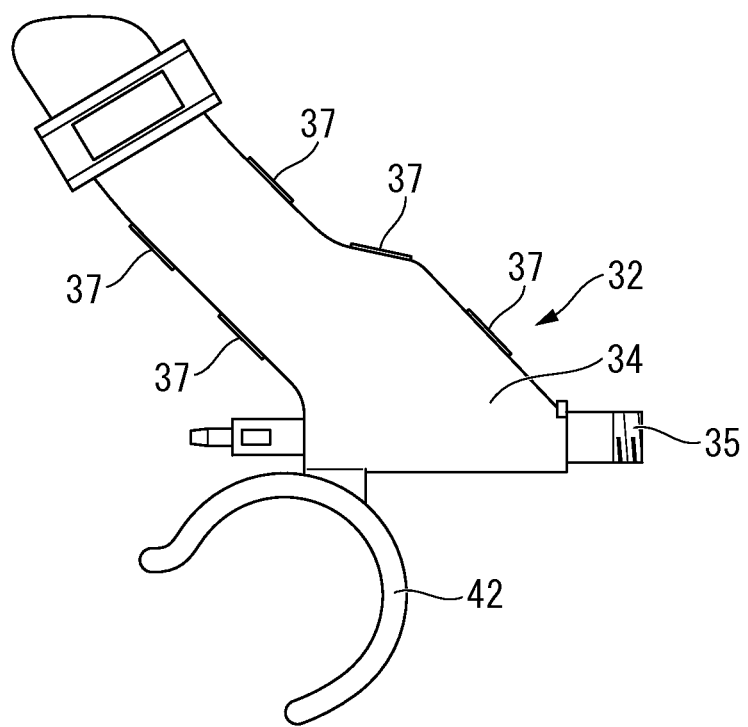
FIG. 8 is a side view illustrating the configuration of a part of guide wire insertion part in the endoscopic treatment system.
Figure 9:
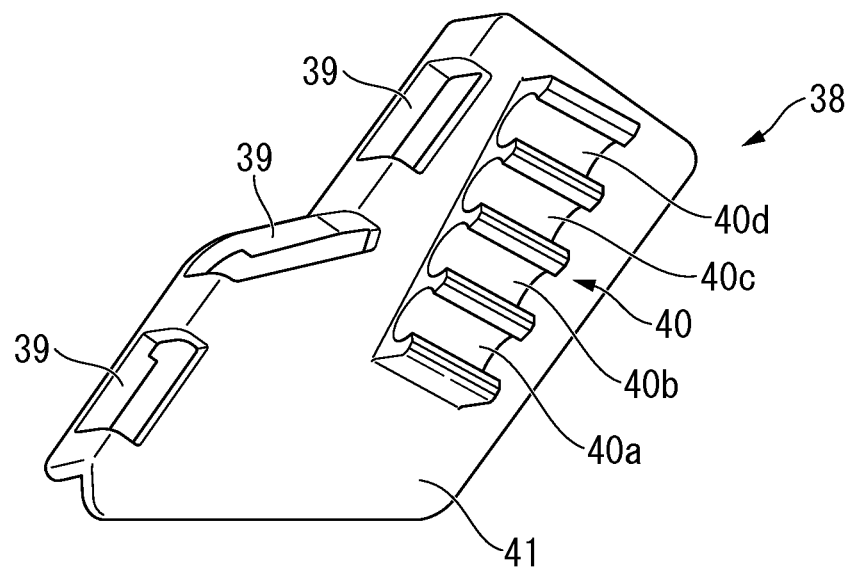
FIG. 9 is a perspective view illustrating a fixing member which is attached to the guide wire insertion part.
Figure 10:
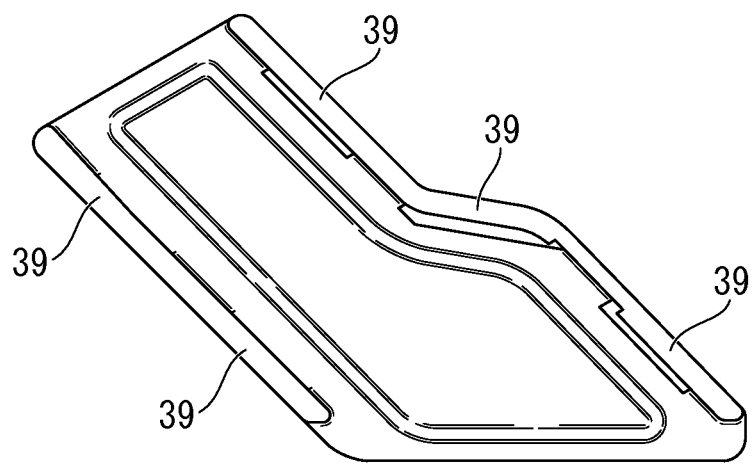
FIG. 10 is a rear view of the fixing member.

FIG. 8 is a side view illustrating the configuration of a part of the guide wire insertion part 34 in the endoscopic treatment system 1. FIG. 9 is a perspective view illustrating a fixing member 38 which is attached to the guide wire insertion part 34. FIG. 10 is a rear view of the fixing member 38.

As illustrated in FIG. 8, the guide wire insertion part 34 has a tubular wire insertion port 35 which communicates with the guide wire tube 33, a connection part 36 which is used to connect the guide wire insertion part 34 to the second operating part 45, and a second connection part 42 which is used to connect the guide wire insertion part 34 to an endoscope apparatus 100.

The connection part 36 is formed to protrude from the outer surface of the wire insertion port 35 in the radial direction of the wire insertion port 35. The connection part 36 has the fixing member 38 (see FIG. 9) which is used to fix the guide wire holder 2 to the operating part 30. As illustrated in FIG. 8, the connection part 36 has protrusions 37 which are used to attach the fixing member 38.

As illustrated in FIGS. 9 and 10, the fixing member 38 has locking parts 39 which are able to be locked to the protrusions 37 formed in the connection part 36, and a concave portion 40 which is engaged with the outer surface of the tube body 3 constituting the guide wire holder 2.

The concave portion 40 provided in the fixing member 38 is engaged with adjacent portions in the tube body 3 wound circumferentially by friction. The concave portion 40 has an arc-like concave shape which covers half or more the circumference of the outer surface of the tube body 3 in the cross-section of the tube body 3 in the radial direction. The concave portion 40 may be engaged with at least one place of the tube body 3 wound circumferentially. That is, at least one concave portion 40 may be provided in the fixing member 38. If the number of concave portions 40 is equal to or greater than two, it is possible to more stably hold the tube body 3. In this embodiment, the concave portion 40 has four adjacent concave portions 40a to 40d.

As illustrated in FIG. 9, in the fixing member 38, the periphery of a portion where the concave portion 40 is formed is a flat planar portion 41. The planar portion 41 is in contact with the outer surface of the tube body 3 (see FIG. 1) and supports the tube body 3 to suppress the shaking of the guide wire holder 2 during the use of the endoscopic treatment system 1.

As illustrated in FIG. 8, the second connection part 42 is formed in a C shape having an arc shape within the same plane passing through the axis of the guide wire insertion part 34. The second connection part 42 is elastic and is engaged with the operating part 102 (see FIG. 18) of the endoscope apparatus 100.

As illustrated in FIG. 5, the second operating part 45 is connected to the proximal end of the multi-lumen tube 13 pulled out from the first branch part 31 through a connector 46. The connector 46 is coaxial with the multi-lumen tube 13 and has a tubular shape. In the connector 46, a connected part 47 to which the connection part 36 formed in the guide wire insertion part 34 is connected is formed. The connected part 47 has unevenness into which the connection part 36 is fitted.

The connector 46 is provided with a deformation part 48 which is freely deformed with respect to the axial direction. The deformation part 48 is provided with the second branch part 50.

The second branch part 50 is provided for branching into the first lumen 14 and the second lumen 15 provided in the multi-lumen tube 13. The second branch part 50 is provided with a slider part 51 which communicates with the first lumen 14, and a liquid feeding part 57 which communicates with the second lumen 15.

The slider part 51 extends in a direction inclined with respect to the axis of the connector 46. The slider part 51 has a substantially rod-like main body 52, and a slider 54 which is able to slide in the longitudinal axis direction of the main body 52. The main body 52 is provided with a scale which becomes an index for confirming the amount of movement of the slider 54, and a finger hooking ring 53.

The proximal end of the knife wire 19 is fixed to the slider 54. The slider 54 is provided with a plug 55 which supplies a high-frequency current to the knife wire 19. The plug 55 is electrically connected to the knife wire 19 inside the slider 54.

The slider 54 is provided with finger hooking rings 56. An operator of the high-frequency incision device 10 inserts his/her fingers into the ring 53 provided in the main body 52 and the rings 56 provided in the slider 54 to operate the slider part 51. That is, the slider 54 is advanced and retracted with respect to the main body 52, thereby moving the knife wire 19 in the longitudinal axis direction of the main body 52. For example, if the slider 54 is moved toward the proximal end side of the main body 52, in the incision part 12 arranged at the distal end of the insertion part 11, the distal end of the multi-lumen tube 13 is pulled to the proximal end side by the knife wire 19, and the distal end of the multi-lumen tube 13 is curved.

The liquid feeding part 57 has a liquid feeding mouthpiece 58 which is connectable to a syringe, and a conduit 59 which communicates with the liquid feeding mouthpiece 58 and the second lumen 15 and in which a liquid flows. In the liquid feeding mouthpiece 58, for example, a protrusion which conforms to a lock type syringe may be formed, or a surface with which a slip chip type syringe is engageable may be formed.

Figure 11:
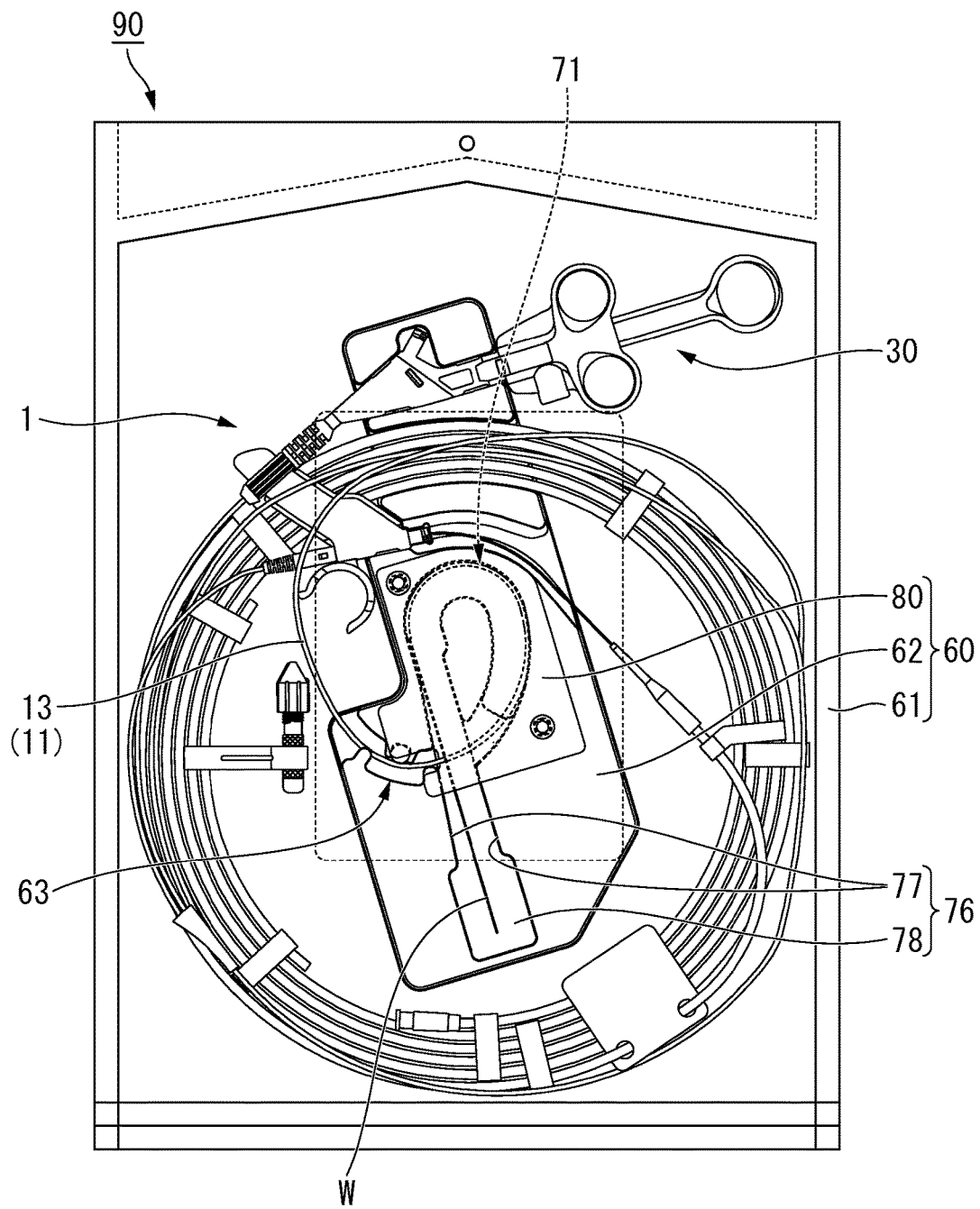
FIG. 11 is a schematic plan view illustrating a state where the endoscopic treatment system is packaged by a packaging material.

Next, the configuration of a packaging material 60 which packages the endoscopic treatment system 1 of this embodiment will be described. FIG. 11 is a schematic plan view illustrating a state where the endoscopic treatment system 1 is packaged by the packaging material 60.

As illustrated in FIG. 11, the packaging material 60 includes a sterilizer pack 61, a tray 62, and a lid member 80.

The sterilizer pack 61 is a sealable bag, and in the sterilizer pack 61, the tray 62 with the lid member 80 attached thereto is stored in a sterilized state with the endoscopic treatment system 1 attached thereto.

Figure 12:
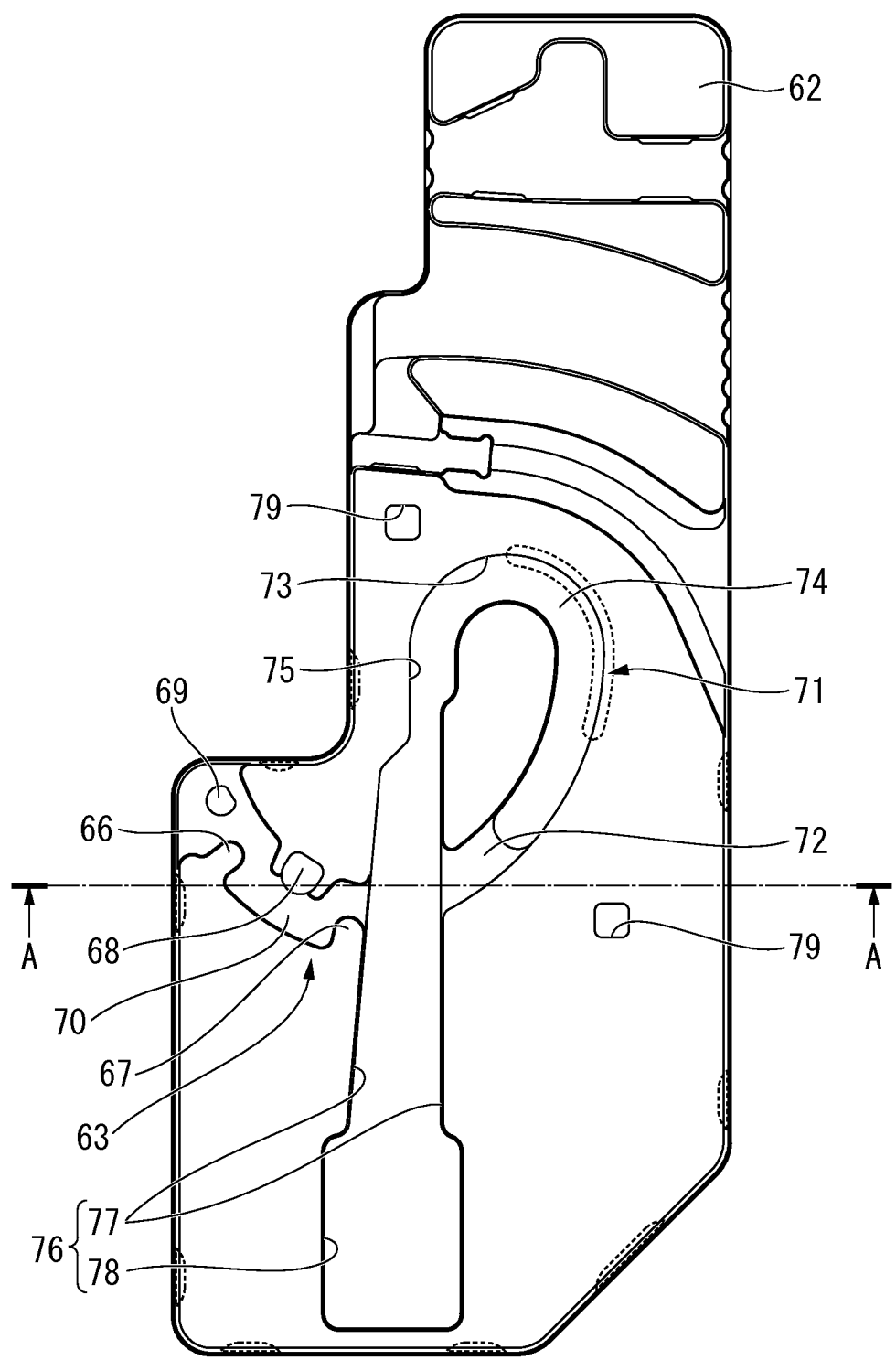
FIG. 12 is a plan view of the packaging material.
Figure 13:
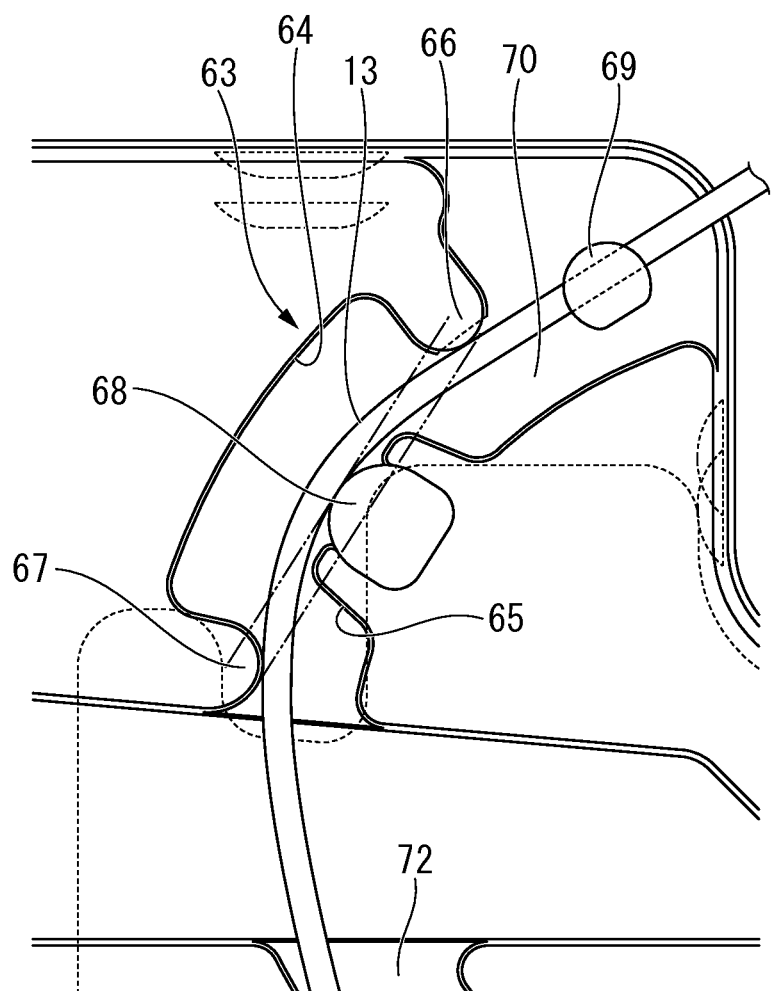
FIG. 13 is an enlarged view of the packaging material.
Figure 15:
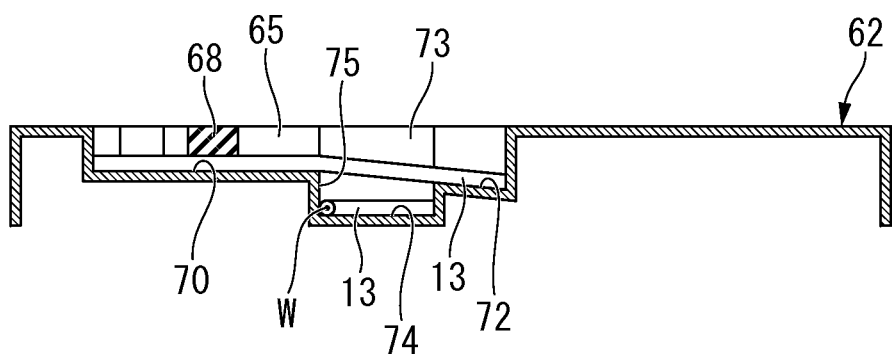
FIG. 15 is a sectional view taken along the line A-A of FIG. 12, and illustrates a state where the endoscopic treatment system is attached.
Figure 16:
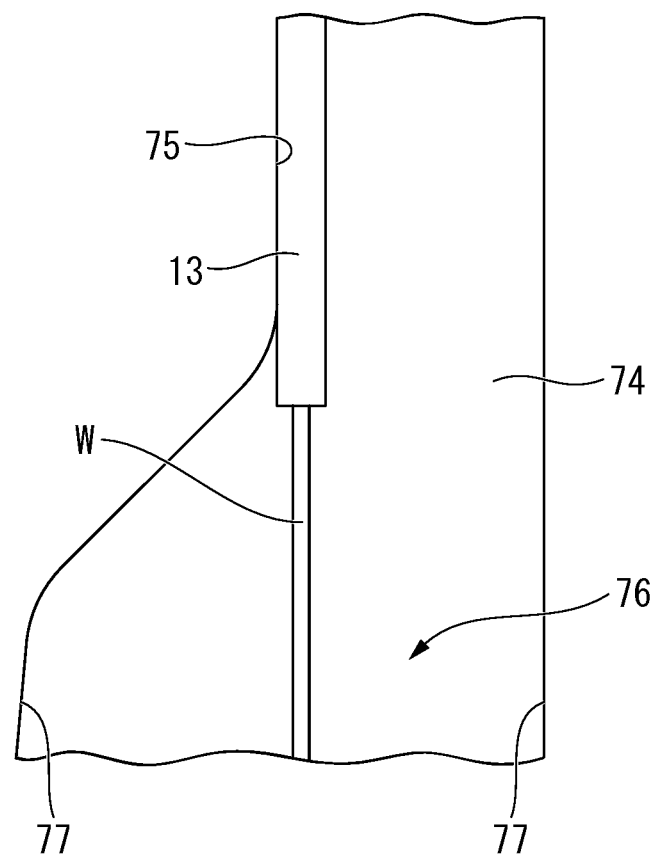
FIG. 16 is an enlarged view of the packaging material, and illustrates a state where the endoscopic treatment system is attached.

FIG. 12 is a plan view of the tray 62 in the packaging material 60. FIG. 13 is an enlarged view of the tray 62 in the packaging material 60. FIG. 14 is a sectional view taken along the line A-A of FIG. 12. FIG. 15 is a sectional view taken along the line A-A of FIG. 12 and illustrates a state where the endoscopic treatment system 1 is attached. FIG. 16 is an enlarged view of the tray 62 in the packaging material 60 and illustrates a state where the endoscopic treatment system 1 is attached.

A plate material to which hydrophilic lubricating coating provided at the distal end of the guide wire W is rarely stuck is molded by pressing or the like to produce the tray 62. For example, the tray 62 is molded using a thin plate material made of polypropylene.

As illustrated in FIGS. 11 and 12, the tray 62 has unevenness to hold the operating part 30 of the high-frequency incision device 10 and the guide wire holder 2 in a predetermined positional relationship.

The tray 62 has a locking part 63 which is used to fix the insertion part 11 of the high-frequency incision device 10 to the tray 62, a pre-curved holding part (sheath holding part) 71 which is used to hold the pre-curved shape of the insertion part 11, and a wire storage part 76 in which the guide wire W is stored in a state where the guide wire W is delivered from the distal end of the third lumen 16 of the insertion part 11.

The locking part 63 has a groove shape which has a substantially U shape and extends toward an introduction part 72 of the pre-curved holding part 71. A first end member 66 and a second end member 67 are formed in a first wall portion 64 which is one of a pair of wall portions facing each other, and an intermediate member 68 is provided in a second wall portion 65 which is the other wall portion of a pair of wall portions.

On the side opposite to the introduction part 72 in the locking part 63, a flap part 69 which is a part of the tray 62 is formed. The first end member 66, the intermediate member 68, the second end member 67, and the flap part 69 are in contact with the outer surface of the multi-lumen tube 13 of the insertion part 11, whereby the insertion part 11 is able to be held toward the introduction part 72 of the pre-curved holding part 71.

The first end member 66 and the second end member 67 are protrusions which are in contact with the outer surface of the multi-lumen tube 13 at two places separated from each other in the longitudinal axis direction of the multi-lumen tube 13 and the substantially same position in the circumferential direction of the multi-lumen tube 13.

The intermediate member 68 is arranged between the first end member 66 and the second end member 67 (in this embodiment, at the substantially center between the first end member 66 and the second end member 67). The intermediate member 68 is an elastic member and is able to be in contact with the outer surface of the multi-lumen tube 13 from the side opposite to the first end member 66 and the second end member 67 in sectional view perpendicular to the longitudinal axis of the multi-lumen tube 13.

The intermediate member 68 is easily deformed by a restoring force to bring the multi-lumen tube 13 into a linear state compared to the first end member 66 and the second end member 67. For this reason, the multi-lumen tube 13 slightly bites into the intermediate member 68, and the multi-lumen tube 13 rarely comes off the locking part 63.

A specific example of the intermediate member 68 is, for example, a silicon tube.

In the tray 62, a portion where the intermediate member 68 is arranged may be formed to hold the intermediate member 68 such that the intermediate member 68 is not shifted. In this case, it is not necessary to bond the intermediate member 68 and the tray 62.

The flap part 69 has a function of pressing the multi-lumen tube 13 such that the multi-lumen tube 13 is arranged along the bottom 70 of the locking part 63. The flap part 69 is able to be deformed by the elasticity of the plate material constituting the tray 62. In this embodiment, the operator performs an operation to pull up the multi-lumen tube 13 from the bottom 70 of the locking part 63, whereby the flap part 69 is able to be elastically deformed to spring up. The flap part 69 springs up, whereby the multi-lumen tube 13 is able to be detached from the flap part 69.

The pre-curved holding part 71 has an introduction part 72, a curved wall 73, a bottom surface 74, and a distal end guide wall 75.

As illustrated in FIGS. 12 and 14, the introduction part 72 is a surface which is inclined downward from the substantially same height as the bottom 70 of the groove of the locking part 63 toward the bottom surface 74 of the pre-curved holding part 71.

As illustrated in FIG. 12, the curved wall 73 is a wall which is placed in the outer portion of the curve of the pre-curved holding part 71 having a curved shape, and has a curved shape which defines the pre-curved shape of the multi-lumen tube 13 from the introduction part 72 toward the distal end guide wall 75.

The bottom surface 74 is a surface which is connected to the introduction part 72 through a step and is perpendicular to the curved wall 73.

The distal end guide wall 75 is a plane which is formed continuously from the curved wall 73, and is a surface which is perpendicular to the bottom surface 74 of the pre-curved holding part 71. As illustrated in FIGS. 15 and 16, the distal end of the multi-lumen tube 13 is linearly arranged in the distal end guide wall 75.

As illustrated in FIGS. 12 and 16, the wire storage part 76 has a groove shape in which the guide wire W exposed from the distal end of the multi-lumen tube 13 is arranged, and has a pair of wall surfaces 77 which have a shape with a gradually opening interval according to the distance from the pre-curved holding part 71, and a distal end storage part 78 which is arranged at a position farthest from the pre-curved holding part 71. In this embodiment, at least the entire portion applied with hydrophilic lubricating coating out of the guide wire W is stored in the wire storage part 76.

The positional relationship and the inclination angle of a pair of wall surfaces 77 of the wire storage part 76 with respect to the distal end guide wall 75 are determined such that the guide wire W is not in direct contact with a pair of wall surfaces 77 or even when the guide wire W is in contact with a pair of wall surfaces 77 of the wire storage part 76, the contact pressure decreases.

The distal end storage part 78 is provided for the sake of preventing the distal end portion of the guide wire W from being in contact with the plate material constituting the tray 62, for example, when a bending habit is applied to the distal end of the guide wire W.

Figure 17:
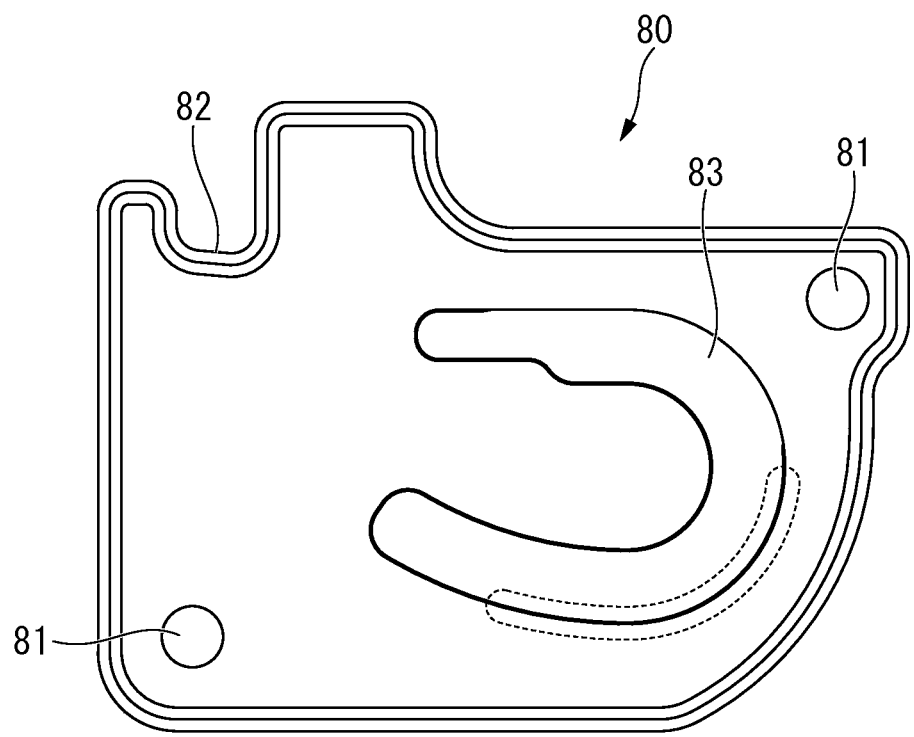
FIG. 17 is a plan view illustrating a lid member in the packaging material.

FIG. 17 is a plan view illustrating the lid member 80 in the packaging material 60.

As illustrated in FIGS. 11 and 17, the lid member 80 covers the pre-curved holding part 71 with a lid and functions as a stopper of the intermediate member 68. The lid member 80 is provided with a protrusion 81 which is used to fix the lid member 80 to the tray 62. In this embodiment, a recess 79 into which the protrusion 81 of the lid member 80 is inserted is formed in the tray 62. The lid member 80 is provided with a notch portion 82 which follows the groove shape of the locking part 63, and while the lid member 80 is fixed to the tray 62, the multi-lumen tube 13 is able to be detached from the locking part 63.

The lid member 80 is provided with a flat top surface portion 83 which faces the bottom surface 74 in the pre-curved holding part 71.

When the lid member 80 has no function as a stopper of the intermediate member 68, the intermediate member 68 may be fixed to the tray 62. When the lid member 80 has no function as a stopper of the intermediate member 68, although the intermediate member 68 is likely to be in contact with the sterilizer pack 61, in this case, unevenness may be formed in the intermediate member 68 such that the intermediate member 68 and the sterilizer pack 61 are not in close contact with each other.

Figure 18:
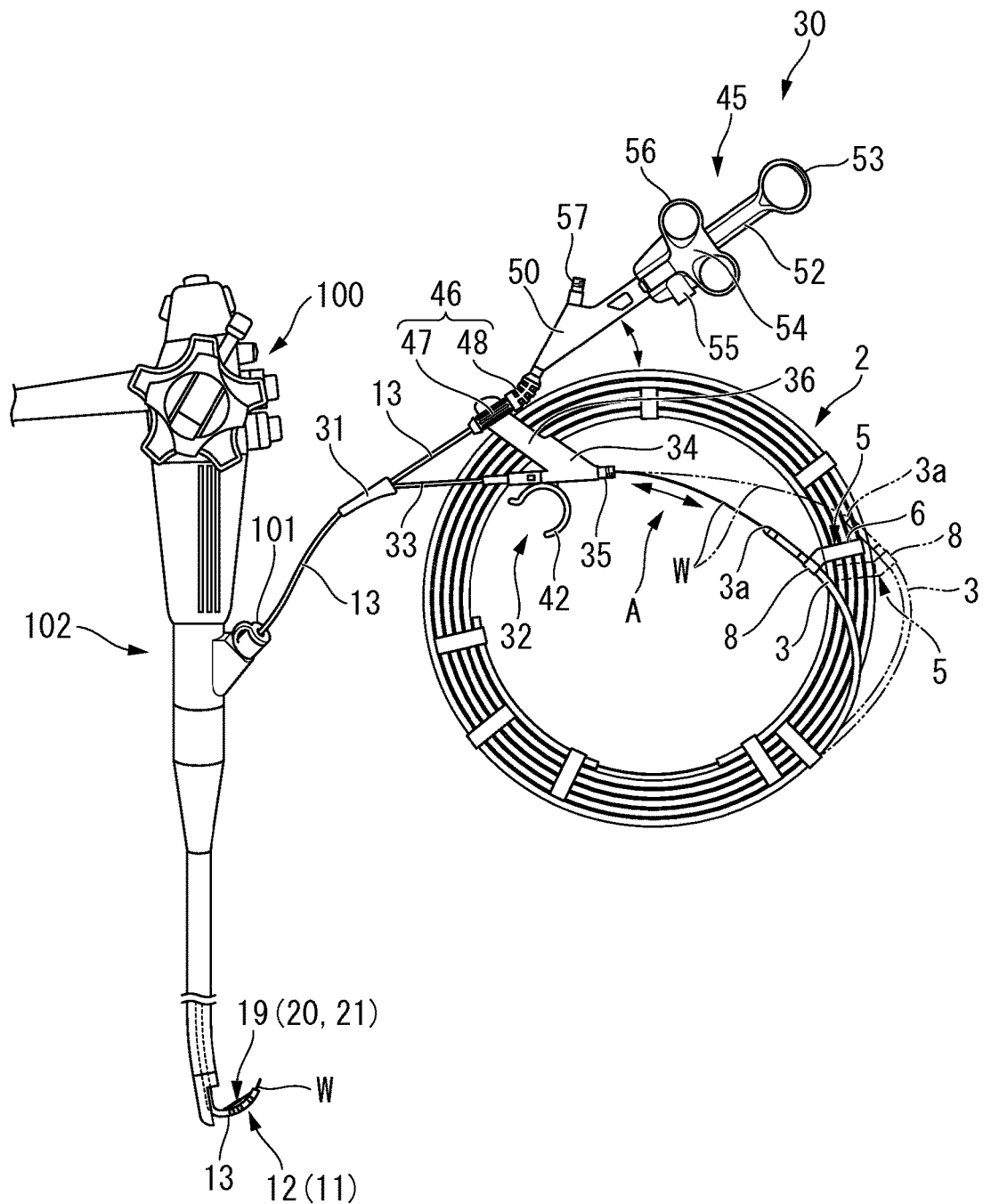
FIG. 18 is an explanatory view for describing the usage of the endoscopic treatment system.
Figure 19:
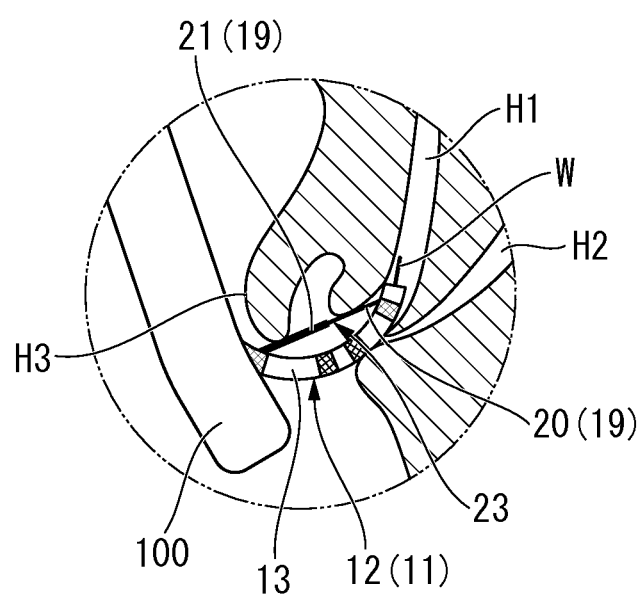
FIG. 19 is a schematic view illustrating a process of an operation using the endoscopic treatment system.

Next, the usage and action of the endoscopic treatment system 1 of this embodiment will be described. In this embodiment, for example, description will be provided as to an operation (EST (duodenal papilla sphincter muscle resection)) which incises a duodenal papilla to discharge cholelith generated in a bile duct into a duodenum. FIG. 18 is an explanatory view for describing the usage of the endoscopic treatment system 1. FIG. 19 is a schematic view illustrating a process of an operation using the endoscopic treatment system 1.

In this embodiment, the endoscopic treatment system 1 is provided as an endoscope system 90 in a state of being stored in the packaging material 60.

As illustrated in FIG. 1, in the endoscopic treatment system 1, the guide wire W is inserted into the third lumen 16 formed in the multi-lumen tube 13 constituting the insertion part 11 in advance, and in a state where the high-frequency incision device 10 is fixed to the guide wire holder 2 by the fixing member 38, the high-frequency incision device 10 and the guide wire holder 2 are fixed to the tray 62. The endoscopic treatment system 1 is stored in the sterilizer pack 61 (see FIG. 11).

As illustrated in FIG. 11, in the holding device 5, the first concave portion 6 is attached to the tube body 3 such that the second concave portion 8 is placed inside the circumference of the tube body 3 in a state where the portion of the opening 3a, through which the guide wire W is delivered from the tube body 3, is fixed to the second concave portion 8.

The endoscopic treatment system 1 is kept in a sterilized state in the sterilizer pack 61 until use in a state where the high-frequency incision device 10 and the guide wire holder 2 are attached integrally. When the endoscopic treatment system 1 is stored in the sterilizer pack 61, the positional relationship in which the second operating part 45 of the high-frequency incision device 10 is adjacent to the guide wire holder 2 is maintained by the tray 62. Specifically, the longitudinal axis of the main body 52 of the second operating part 45 is directed in the direction normal to the tube body 3 wound circumferentially in the guide wire holder 2. In this way, the endoscopic treatment system 1 is wound compact at the time of the storage in the sterilizer pack 61.

During the use of the endoscopic treatment system 1, first, the sterilizer pack 61 is opened, and the tray 62 to which the high-frequency incision device 10 and the guide wire holder 2 are fixed is removed from the sterilizer pack 61 (Step S1). At this time, the lid member 80 is fixed to the tray 62, and the distal end portion of the multi-lumen tube 13 of the insertion part 11 of the high-frequency incision device 10 and the distal end portion of the guide wire W is not released from the tray 62 by the lid member 80 and the locking part 63. Since the insertion part 11 is held by the flap part 69, when the operator does not apply a force to open the flap part 69, the multi-lumen tube 13 of the insertion part 11 is pressed against the bottom 70 of the locking part 63 by the flap part 69.

Subsequently, the operating part 30 and the guide wire holder 2 are detached from the tray 62, the multi-lumen tube 13 is released from the flap part 69, and the multi-lumen tube 13 is released from the first end member 66, the second end member 67, and the intermediate member 68 of the locking part 63 (Step S2).

Subsequently, the insertion part 11 arranged in the gap between the tray 62 and the lid member 80 is pulled out (Step S3). With this, the high-frequency incision device 10 is released from the tray 62.

Next, an example of the usage of the endoscopic treatment system 1 will be described.

First, for the endoscopic treatment system 1 detached from the tray 62, the operator inserts his/her fingers into the rings 53 and 56 provided in the second operating part 45 to hold the second operating part 45 (Step S3). In Step S3, a preferred way to use is to place the guide wire holder 2 below the second operating part 45. That is, the guide wire holder 2 is attached to the operating part 30 in a state of hanging from the operating part 30. In this way to hold, the deformation part 48 is curved by the weight of the guide wire holder 2 itself, and the guide wire holder 2 is separated from the operating part 30 compared to the storage of the endoscopic treatment system 1 (see FIGS. 11 and 18). With this, the space around the operating part 30 is widened.

A high-frequency power supply device (not shown) which is used to supply a high-frequency current to the knife wire 19 is connected to the plug 55 provided in the operating part 30.

The operator inserts the distal end of the insertion part 11 into a treatment device channel 101 of the endoscope apparatus 100, and causes the insertion part 11 to protrude from the distal end of the treatment device channel 101. The guide wire W is pushed toward the distal end of the insertion part 11. At this time, the operator advances and retracts the guide wire W with an expose portion (a portion indicated by a symbol A in FIG. 18) between a wire insertion port 35 provided in the operating part 30 and the opening 3a in the tube body 3, through which the guide wire W is delivered, out of the full length of the guide wire W.

If necessary, the position of the opening 3a in the tube body 3, through which the guide wire W is delivered, may be changed outside the outermost circumference of the tube body 3 wound circumferentially. The position of the opening 3a is able to be changed by changing the attachment direction of the first concave portion 6 to the tube body 3.

As illustrated in FIG. 18, when the opening 3a is placed further inside the innermost circumference of the tube body 3 wound circumferentially, the opening 3a is placed near the wire insertion port 35 placed inside the circumference, and the opening 3a faces the wire insertion port 35. With this, the distance between the wire insertion port 35 and the opening 3a is short, and the curvature of the guide wire W which is exposed between the wire insertion port 35 and the opening 3a is able to be reduced. Therefore, the guide wire W is rarely buckled when moving the guide wire W, and the guide wire W is able to be moved smoothly.

Conversely, when the opening 3a is placed further outside than the outermost circumference of the tube body 3 wound circumferentially, the length of the exposed guide wire W is increased compared to a case where the opening 3a is placed inside the circumference. With this, the length of the guide wire W which is able to be moved by one operation is increased compared to a case where the opening 3a is placed inside the circumference.

As illustrated in FIG. 19, the operator causes the guide wire W to protrude from the distal end of the insertion part 11 and inserts the guide wire W into the duodenal papilla. The operator pushes the guide wire W while adjusting the position of the guide wire W such that the distal end of the guide wire W enters the bile duct. Subsequently to the guide wire W inserted into the duodenal papilla, the distal end of the insertion part 11 is inserted into the duodenal papilla. The exposed portion 23 of the knife wire 19 is arranged near a sphincter muscle to supply the high-frequency current to the knife wire 19. Then, a biological tissue which is in contact with the exposed portion 23 of the knife wire 19 is incised. The operator moves the slider 54 to the proximal end side of the main body 52, and causes a region on the distal end side in the multi-lumen tube 13 to be curved. With this, the sphincter muscle in a duodenal papilla H3 is cut by the exposed portion 23 of the knife wire 19, and an opening which is required to remove cholelith from a bile duct H1 is formed in the duodenal papilla H3.

When a pancreatic duct H2 is to be treated, the guide wire W is inserted into the pancreatic duct H2.

In this embodiment, since the distal end portion of the guide wire W applied with hydrophilic lubricating coating is stored in the packaging material 60 in a state of being delivered from the distal end of the multi-lumen tube 13 and being separated from the outer surface of the tray 62, hydrophilic lubricating coating of the guide wire W is not stuck to the multi-lumen tube 13 or the tray 62 until the endoscopic treatment system 1 is used after the endoscopic treatment system 1 is stored in the packaging material 60.

In the related art, in order to hold a pre-curved shape in a tube having a lumen, a member, such as a core bar, may be inserted into the lumen. However, when a member, such as a core bar, is inserted into the lumen to maintain the pre-curved shape, it is necessary that the guide wire is retracted from a portion where the core bar or the like is arranged in the lumen, and as described above, in a state where the distal end portion of the guide wire W is delivered from the distal end of the multi-lumen tube 13, it is not possible to maintain a pre-curved shape using a core bar or the like used in the related art.

In contrast, in this embodiment, since the pre-curved shape of the distal end portion of the multi-lumen tube 13 is defined by the pre-curved holding part 71, an additional member which is used to maintain a pre-curved shape is not required. In this embodiment, since it should suffice that only operation to detach the multi-lumen tube 13 from the tray 62 is performed, compared to a case where a member, such as a core bar, is inserted into, for example, the multi-lumen tube 13 to hold a pre-curved shape and removed during the use, the work is simplified.

The wire storage part 76 has a pair of wall surfaces 77 having a clearance from the guide wire W in a state where the multi-lumen tube 13 is attached to the pre-curved holding part 71. For this reason, in this embodiment, even when hydrophilic lubricating coating is provided in the distal end portion of the guide wire W, it is possible to reduce a possibility that hydrophilic lubricating coating is stuck to the wire storage part 76.

In this way, in this embodiment, it is possible to achieve both preventing sticking of coating of the distal end portion of the guide wire W and maintaining the pre-curved shape of the distal end portion of the multi-lumen tube 13.

Since the pre-curved holding part 71 which defines the pre-curved shape of the multi-lumen tube 13 has the curved wall 73, a local pressing force is rarely applied to the pre-curved portion of the multi-lumen tube 13 in a state where the multi-lumen tube 13 is fixed to the tray 62, and the multi-lumen tube 13 follows the surface of the curved wall 73 by a restoring force to bring the multi-lumen tube 13 in a linear state.

Since the introduction part 72 of the pre-curved holding part 71 is a surface which is inclined toward the bottom surface 74 of the pre-curved holding part 71, the multi-lumen tube which extends from the pre-curved holding part 71 to the distal end guide wall 75 along the curved wall 73 is stably held by the bottom surface 74 of the pre-curved holding part 71 and the curved wall 73.

In this embodiment, the endoscopic treatment system 1 is fixed to the tray 62 in a compact state where the second operating part 45 is placed near the guide wire holder 2.

In the endoscopic treatment system 1 of this embodiment, since the main body 52 and the slider 54 of the second operating part 45 in the operating part 30 are placed further outside than the outermost circumference of the tube body 3 wound circumferentially, the tube body 3 is rarely in contact with the hand of the operator during the use of the endoscopic treatment system 1, and the tube body 3 rarely becomes an obstacle.

In this embodiment, when the second operating part 45 is held by a suitable way to hold the second operating part 45 in the endoscopic treatment system 1, the guide wire holder 2 hangs from the operating part 30, and the guide wire holder 2 is separated from the operating part 30 by the weight of the guide wire holder 2 itself. From this point, the tube body 3 is rarely in contact with the hand of the operator during the use of the endoscopic treatment system 1, and the tube body 3 rarely becomes an obstacle.

The deformation part 48 provided in the connector 46 is curved, and the distance between the guide wire holder 2 and the operating part 30 is opened. In this way, the second operating part 45 and the fixing member 38 are connected through the deformable deformation part 48, whereby a compact state where the second operating part 45 is placed near the guide wire holder 2 is maintained at the time of the storage of the endoscopic treatment system 1 and the second operating part 45 is separated from the guide wire holder 2 such that the guide wire holder 2 does not become an obstacle during the use of the endoscopic treatment system 1. That is, the endoscopic treatment system 1 of this embodiment is able to be stored compact, and satisfactory operability during the use is achieved.

During the use of the endoscopic treatment system 1, it is possible to appropriately switch between a positional relationship in which the guide wire W is rarely buckled by the holding device 5 attached to the guide wire holder 2 and a positional relationship in which the amount of movement of the guide wire W which is able to be moved by one operation is able to be increased.

Since the wire insertion port 35 is placed further inside the innermost circumference in the tube body 3 wound circumferentially, the endoscopic treatment system 1 is able to be stored in the sterilizer pack 61 compact compared to a case where the wire insertion port 35 is placed further outside the outer circumference in the tube body 3 wound circumferentially.

The operating part 30 and the guide wire holder 2 are able to be attached and detached by the engagement of the concave portion 40 of the fixing member 38 and the tube body 3. For this reason, when the operating part 30 and the guide wire holder 2 are held and used by different operators, the engagement state of the concave portion 40 and the tube body 3 is released, whereby the operating part 30 and the guide wire holder 2 are able to be used without being fixed.

The position of the opening 3a, through which the guide wire W is delivered by the second concave portion 8 is able to be switched further inside or outside than the tube body 3. For this reason, when the operating part 30 and the guide wire holder 2 are used without being fixed, the operating part 30 and the guide wire holder 2 are able to be used while the opening 3a is placed at an easy-to-operate position.

Although the preferred examples of the invention have been described, the invention is not limited to these examples. Addition, omission, replacement, and other changes of the configuration may be made without departing from the spirit and scope of the invention.

Figure 20:
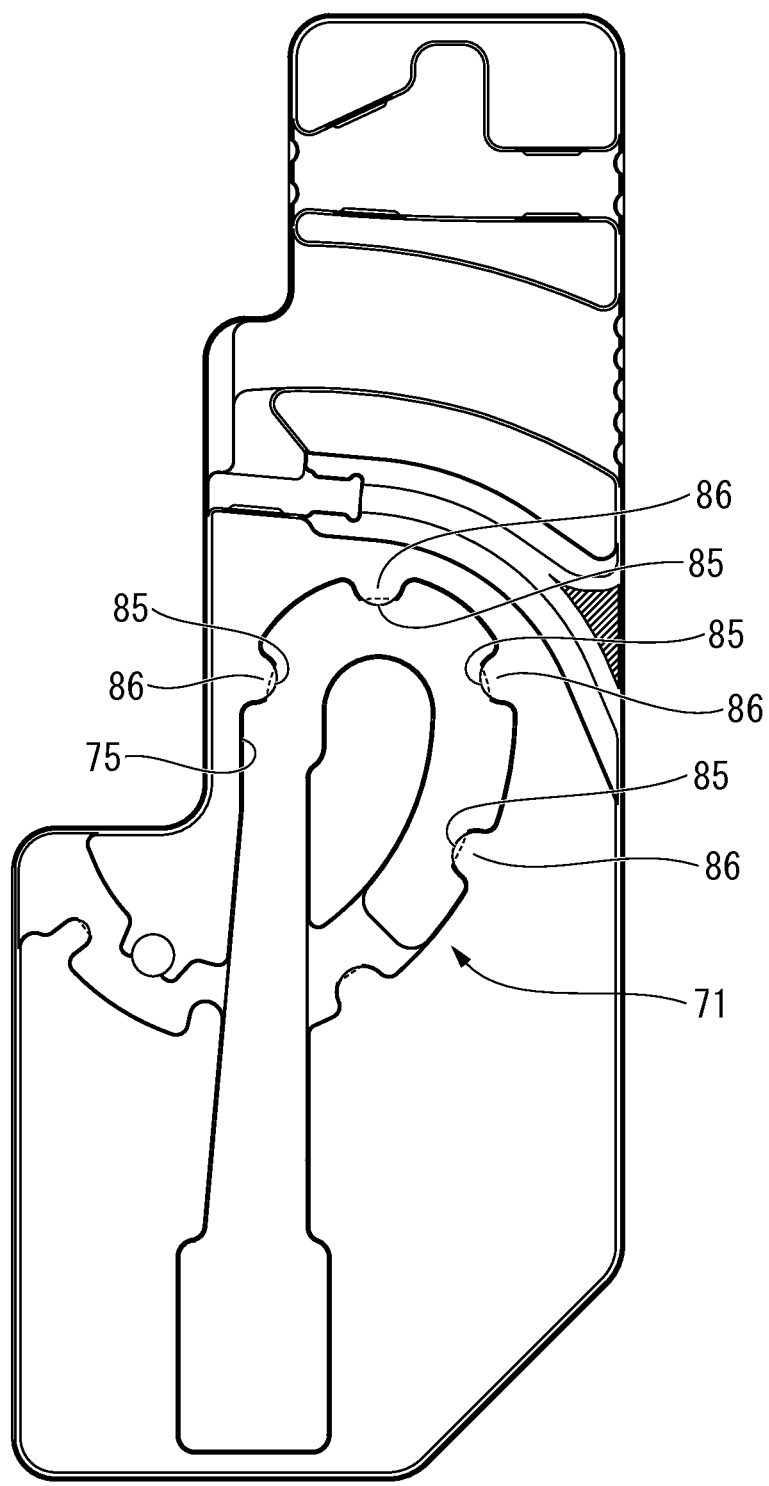
FIG. 20 is a plan view illustrating the configuration of a modification example of the packaging material.

For example, as illustrated in FIG. 20, instead of the curved wall 73 described in the above-described embodiment, the outer surface of the multi-lumen tube 13 may be supported by a plurality of protrusions 86 having claws 85 as a stopper.

For example, the planar portion formed in the fixing member may be provided to be flush with the bottom of the concave portion formed in the fixing member. In this case, the tube body is more stably held by the planar portion which is flush with the bottom of the concave portion, and the guide wire holder rarely shakes.

In the above-described embodiment, the tube body of the guide wire holder is softer than the fixing member and the holding device. The tube body is elastically deformed and is attached to the fixing member or the holding device. Alternatively, the tube body of the guide wire holder may be harder than the fixing member and the holding device. In this case, the tube body may be provided with joints which allow the tube body to be curved to change the direction of the opening, through which the guide wire is delivered.

The tube body of the guide wire holder may have a portion softer than the fixing member and the holding device and a portion harder than the fixing member and the holding device.

In the above-described embodiment, the tray which stores the distal end portion of the guide wire and the tube body of the guide wire holder are separately provided. Alternatively, a storage part which stores the distal end portion of the guide wire may be configured integrally with the tube body of the guide wire holder.

Figure 21:
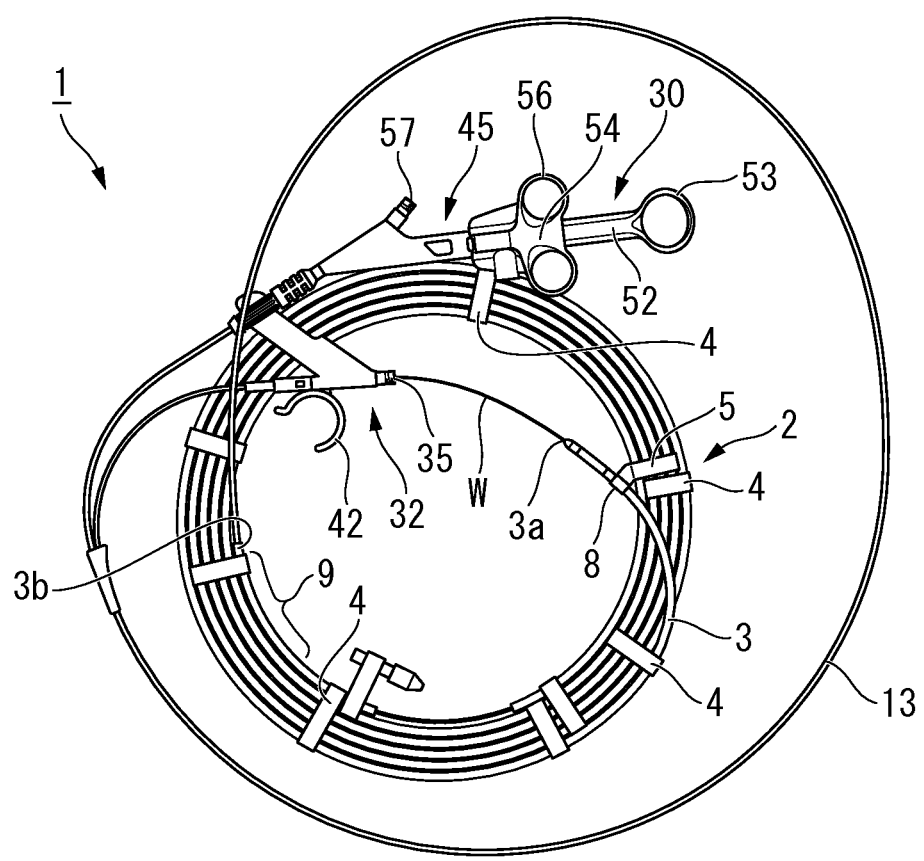
FIG. 21 is a plan view illustrating another configuration example of this embodiment.

Specifically, as illustrated in FIG. 21, a proximal end-side storage part 9 may be provided in an end portion 3b opposite to the distal end-side opening, from which the guide wire of the tube body 3 of the guide wire holder 2 protrudes.

The guide wire W which protrudes from the distal end of the tube body 3 in the guide wire holder 2 is delivered from the distal end of the multi-lumen tube 13 through the multi-lumen tube 13. The distal end portion of the guide wire W delivered from the distal end of the multi-lumen tube 13 is stored in the proximal end-side storage part 9 of the guide wire holder 2.

Although the preferred embodiments of the invention have been described, the invention is not limited to these embodiments. Addition, omission, replacement, and other changes of the configuration may be made without departing from the spirit and scope of the invention.

The invention is not limited to the above description and is limited only by the appended claims.

What is claimed is:

1. A packaging material packaging an endoscopic treatment system to be used in combination with an endoscope, wherein the endoscopic treatment system includes:
   an endoscopic treatment device includes:
      an operating part with a distal end and a proximal end; and
      a sheath which is connected to the distal end of the operating part and in which a lumen is formed; and
      a guide wire which has a coated region applied with coating at a distal end of the guide wire and is inserted into the lumen of the sheath, and
   wherein the packaging material includes:
      a tray which holds a distal end side of the sheath in a state where a predetermined positional relationship between the sheath and the guide wire is held and the coated region of the guide wire is exposed from a distal end of the sheath;
      wherein the tray includes:
         a sheath holding part configured to hold the sheath; and
         a wire storage part placed closer to the distal end side of the sheath than the sheath holding part, and configured to hold the full length of the coated region of the guide wire exposed from the distal end of the sheath straight,
         wherein the sheath holding part includes:
            an introduction part positioned at a proximal end of the sheath; and
            a bottom surface positioned closer to the distal end of the sheath than the introduction part, wherein the bottom surface is positioned lower than the introduction part in a depth direction of the tray.

2. The packaging material according to claim 1, wherein the sheath holding part has a curved shape which holds the distal end side of the sheath in a curved state, and wherein the introduction part is positioned at a proximal end side of the curved shape.

3. The packaging material according to claim 2, wherein the wire storage part is arranged so as to intersect, with a part of the sheath that is closer to the proximal end of the sheath than the sheath holding part of the sheath, and wherein the sheath holding part holds the sheath so that the part of the sheath passes through over the guide wire that is stored in the wire storage part.

4. The packaging material according to claim 1, wherein the tray includes:
   a locking portion positioned closer to the proximal end of the sheath than the introduction part, wherein the locking portion is configured to lock the sheath so as to be detachable with respect to the depth direction of the tray.

5. The packaging material according to claim 4, wherein the tray includes:
   a distal end guide wall which extends from the sheath holding part and against which a distal end portion of the sheath is pressed by a restoring force to bring the sheath into a linear state, wherein the wire storage part includes a pair of wall surfaces which extend from the distal end guide wall and gradually increases in an interval between the pair of wall surfaces according to the distance from the distal end guide wall, and wherein the pair of wall surfaces are separated from the guide wire in a state where the distal end of the guide wire is arranged between the pair of wall surfaces.

6. The packaging material according to claim 5, wherein the distal end guide wall has a planar shape configured to hold the distal end portion of the sheath straight.

7. The packaging material according to claim 6, wherein the wire storage part is formed of polypropylene.

8. The packaging material according to claim 7, wherein the pair of wall surfaces extend from the bottom surface, and wherein the packaging material further includes a lid member which has a top surface portion facing the bottom surface.

9. The packaging material according to claim 8, wherein the endoscopic treatment system further includes:
   a guide wire holder in which a tube body in which the guide wire is stored is wound circumferentially; and
   a fixing member configured to connect the operating part to the guide wire holder such that the distal end and the proximal end of the operating part of the endoscopic treatment device are placed outside the circumference of the guide wire holder, and wherein the tray is configured to support the operating part and the guide wire holder in a state where a predetermined positional relationship between the operating part and the guide wire holder is held.

10. The packaging material according to claim 9, wherein the sheath holding part and the wire storage part are positioned inside of a circumference of a circle of the guide wire holder in a state where the tray holds the operating part and the guide wire holder.

* * * * *